United States Patent
Hardcastle, III et al.

(10) Patent No.: US 8,670,938 B2
(45) Date of Patent: Mar. 11, 2014

(54) METHODS AND APPARATUS FOR ACCURATE SERVICE LIFE PREDICTION

(75) Inventors: Henry K. Hardcastle, III, Phoenix, AZ (US); Richard Schultz, Niles, IL (US)

(73) Assignee: Atlas Materials Testing Technologies, LLC, Chicago, IL (US)

( * ) Notice: Subject to any disclaimer, the term of this patent is extended or adjusted under 35 U.S.C. 154(b) by 495 days.

(21) Appl. No.: 13/042,225

(22) Filed: Mar. 7, 2011

(65) Prior Publication Data

US 2011/0224905 A1 Sep. 15, 2011

Related U.S. Application Data

(60) Provisional application No. 61/312,472, filed on Mar. 10, 2010.

(51) Int. Cl.
*G01W 1/00* (2006.01)

(52) U.S. Cl.
CPC ............................ *G01W 1/00* (2013.01)
USPC ............................................. 702/3

(58) Field of Classification Search
USPC ............... 702/3, 117, 118, 182–185
See application file for complete search history.

(56) References Cited

U.S. PATENT DOCUMENTS

| | | |
|---|---|---|
| 5,503,032 A | 4/1996 | Tikhtman et al. |
| 5,646,358 A | 7/1997 | Tikhtman et al. |
| 6,720,562 B2 | 4/2004 | Rathod et al. |
| 6,872,936 B2 | 3/2005 | Rathod et al. |
| 6,946,652 B2 | 9/2005 | Rathod et al. |
| 7,038,196 B2 | 5/2006 | Scott et al. |
| 2002/0139928 A1* | 10/2002 | Rathod et al. ............ 250/252.1 |
| 2005/0167580 A1 | 8/2005 | Scott et al. |
| 2007/0295114 A1 | 12/2007 | Pilcher et al. |
| 2010/0005911 A1 | 1/2010 | Scott et al. |

OTHER PUBLICATIONS

Wikipedia entry, "Fuzzy Logic," retrieved from http://en.wikipedia.org/wiki/Fuzzy_logic on Mar. 2, 2011, last modified Mar. 1, 2011, 9 pages.
G 155 "Exposure Conditions" Section X3.1, 1 page.
ASTM International, Designation: G154-06, "Standard Practice for Operating Fluorescent Light Apparatus for UV Exposure of Nonmetallic Materials," Jun. 5, 2006, 11 pages.
1998 Annual Book of ASTM Standards, General Methods and Instrumentation, vol. 14.02, Section 14, pp. 1258-1267 (13 pages).

(Continued)

*Primary Examiner* — Edward Raymond
(74) *Attorney, Agent, or Firm* — Vedder Price P.C.

(57) ABSTRACT

Methods and apparatus for accurate service life prediction by exposing a test specimen to operating parameters of a multi-variable micro-environment cycle in an accelerated weathering test apparatus including an irradiance source, a temperature adjustment source and a moisture adjustment source connected to a controller to: expose the test specimen to the operating parameters of the multi-variable micro-environment cycle recreated in the test chamber; monitor the exposure of the test specimen to the multi-variable micro-environment cycle to generate run-time variables; and adjust the run-time variables to reconcile to the operating parameters.

71 Claims, 6 Drawing Sheets

(56) References Cited

OTHER PUBLICATIONS

Richard Ghez, "A Primer of Diffusion Problems," 1988, pp. 86-89, John Wiley & Sons, Inc., New York (4 pages).

Crank et al., "Diffusion in Polymers," Academic Press, London 1968, 6 pages.

Wikipedia entry, "Fuzzy Logic," retrieved from http://en.wikipedia.org/wiki/Fuzzy_logic on Mar. 2, 2011, last modified Mar. 1, 2011, 9 pages, 2011.

"Accelerated Exposure of Automotive Exterior Materials Using a Controlled Irradiance Water-Cooled Xenon Arc Apparatus", REV. Oct. 2004, 16 pages.

* cited by examiner

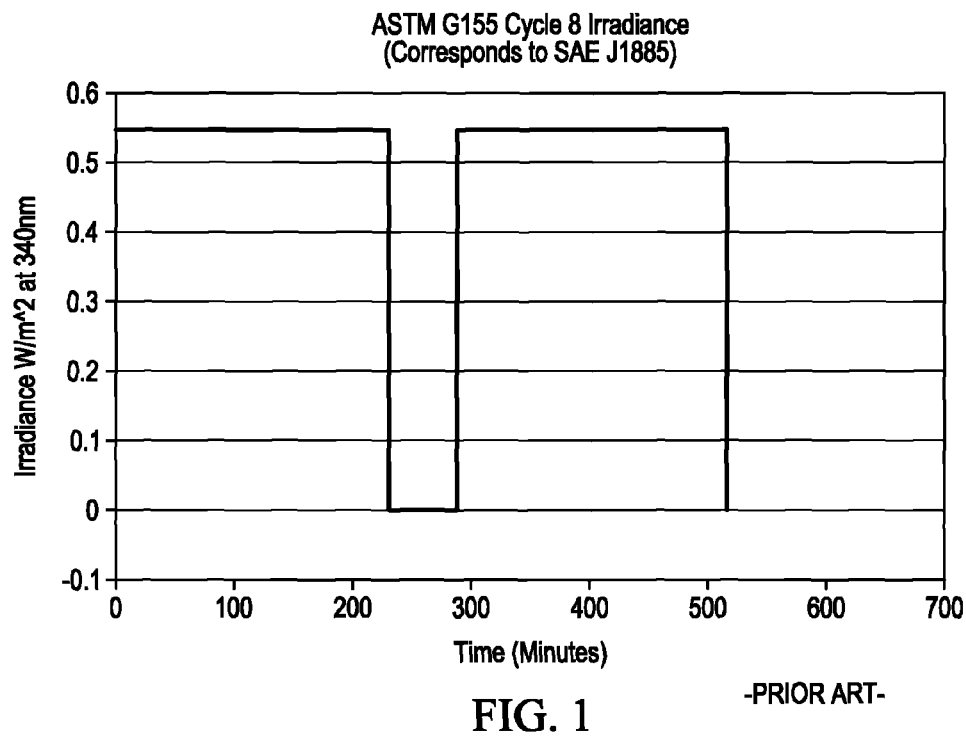
FIG. 1 -PRIOR ART-
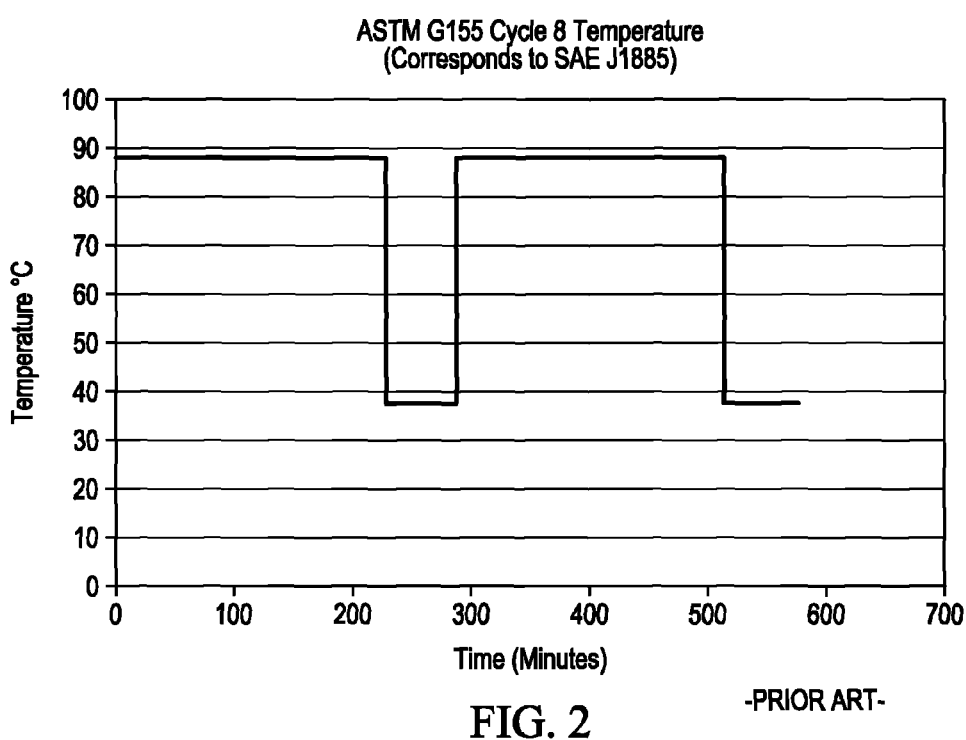
FIG. 2 -PRIOR ART-

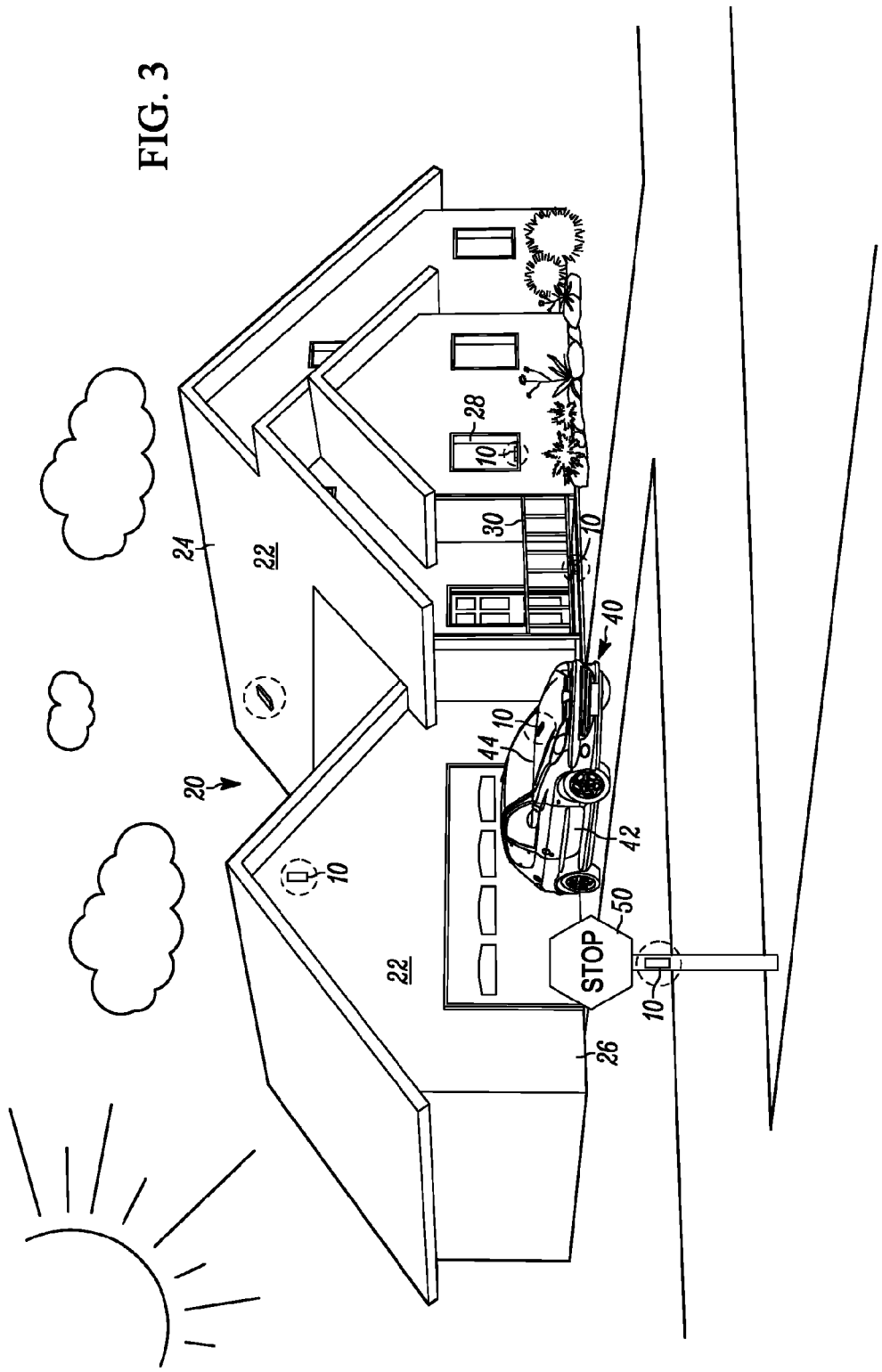

METHODS AND APPARATUS FOR ACCURATE SERVICE LIFE PREDICTION

FIELD OF THE DISCLOSURE

The present disclosure is related to methods and apparatus for accurate service life prediction, and more particularly, to methods and apparatus for accurate service life prediction by exposing a test specimen to operating parameters of a multi-variable micro-environment cycle recorded in-situ in an accelerated weathering test apparatus including a light source, other than solar radiation.

BACKGROUND

For a long time, scientists in the field of material science have researched, designed and tested various instruments that claimed to provide accurate service life prediction ("SLP") using accelerated methods. Materials formulators or manufacturers desire to use short term laboratory test methods and apparatus to predict how specific material formulations will perform in an end-use environment before making investments in manufacturing and production and subsequent placement in such end-use environment. The short term laboratory testing needs to be done accurately in order to predict the service life of specific formulations. With such testing, materials scientists can disqualify poor performing material formulations and focus research and design assets (time, money, etc.) on only good performing candidate material formulations. Additionally, material scientists can refrain from costly "overly engineered" materials formulations for specific end uses. In this way, accurate accelerated SLP methods and apparatus can allow the material scientist to look into the future and see how a material will perform under the action of long term weathering degradation processes before actually subjecting a material to years and years of outdoor weathering in an end-use environment.

Currently, there have been long felt and un-met needs in the material science industry to develop an accurate SLP methods and apparatus that faithfully predict material performance in selected or desired micro-environment cycles, notwithstanding the many scientific attempts that have been previously made. For example, the National Institute of Standards & Technology ("NIST") SLP publications and SLP consortiums, leading materials manufacturers' research and development efforts, European and Asian SLP symposium efforts, etc. evidence and document this need as well as the sizeable body of general technical literature on this subject. There also exists a material testing industry commonly referred to as 'weathering testing' that produces instruments that use accelerated laboratory or artificial weathering approaches based on exposure conditions established by standards committees, such as ASTM, NIST, Society of Automotive Engineers ("SAE"), etc., in an attempt at SLP. Even more specifically, there is an American Society for Testing and Materials ("ASTM") standard for SLP that clearly documents the current state of the art for accelerated artificial weathering SLP. Although the current state of the art offers some approaches for SLP, these approaches are found to be significantly and importantly lacking in accuracy and applicability because they fail to recreate desired or selected end-use environments actually experienced by the material. Typically, these approaches offer only qualitative or relative assessments ("good" vs. "poor" predicted performance) or relative ranking (formulation "A" should perform better than formulation "B" in the same end-use environment). Additionally, these approaches typically work in a limited sense for some materials but not for other materials. For example, one SLP approach may be relatively accurate for generally predicting polycarbonate yellowing outdoors (to the degree described herein), but cannot accurately predict to any degree nylon's mechanical properties changes due to end-use environments or be accurate for many other materials or properties.

These approaches provide only meager incremental improvements in SLP and still ultimately fail to accurately predict service life in actual end-use environments for nearly all materials. The solution to accurate SLP, therefore, remains not obvious.

Conventional artificial or laboratory weathering devices use a number of approaches in an attempt to provide meaningful information and attempt to solve the SLP problem. For example, it is conventional knowledge that much of the end-use environment material degradation is caused by solar ultra-violet ("UV") energy degradation, so materials researchers have exposed materials to increased irradiance levels of UV. However, other end-use environment conditions also effect material degradation, such as temperature and moisture. Consequently, researchers also developed test approaches to simultaneously increase UV irradiance, temperature and moisture in weathering testing devices. Examples of conventional state of the art weathering approaches for SLP are set forth in the table below.

TABLE I

| ASTM G 155 COMMON EXPOSURE CONDITIONS | | | |
|---|---|---|---|
| CYCLE | FILTER | IRRADIANCE, APPROX. | EXPOSURE CYCLE |
| 1 | Daylight | 0.35 W/m$^2$/nm. 340 nm | 102 min light at 63 (+−2.5)° C. Black Panel Temperature 18 min light and water spray (air temp. not controlled) |
| 2 | Daylight | 0.35 W/m$^2$/nm. 340 nm | 102 min light at 63 (+−2.5)° C. Black Panel Temperature 18 min light and water spray (air temp. not controlled); 6 h at 95 (+−4.0)% RH, at 24 (+−2.5)° C. Black Panel Temperature |
| 3 | Daylight | 0.35 W/m$^2$/nm. 340 nm | 1.5 h light at 70 (+−5)% RH, at 77 (+−3)° C. Black Panel Temperature .5 h light and water spray (air temp. not controlled) |
| 4 | Window Glass | .30 W/m$^2$/nm. 340 nm | 100% light, 55 (+−5.0)% RH, at 55 (+−2.)° C. Black Panel Temperature |
| 5 | Window Glass | 1.1 W/m$^2$/nm. 420 nm | 102 min light, 35 (+−5.0)% RH, at 63 (+−2.5)° C. Black Panel Temperature 18 minutes light & water spray (air temp. not controlled) |

TABLE I-continued

ASTM G 155 COMMON EXPOSURE CONDITIONS

| CYCLE | FILTER | IRRADIANCE, APPROX. | EXPOSURE CYCLE |
|---|---|---|---|
| 6 | Window Glass | 1.10 $W/m^2/nm$. 420 nm | 3.8 h light at 35 (+−5.0)% RH, at 63 (+−2.5)° C. Black Panel Temperature<br>1 h dark, 90 (+−5.0)% RH, at 43 (+−2)° C. Black Panel Temperature |
| 7 | Daylight | 0.55 $W/m^2/nm$. 340 nm | 40 min light, 50 (+−5.0)% RH, at 70 (+−2)° C. Black Panel Temperature<br>20 min light and water spray on specimen face;<br>60 min light, 50 (+−5.0)% RH, at 70 (+−2)° C. Black Panel Temperature;<br>60 min dark and water spray on specimen back, 95 (+5.0)% RH, 38 (+−2)° C. Black Panel Temperature |
| 8 | Daylight | 0.55 $W/m^2/nm$. 340 nm | 3.8 h light, 50 (+− 5.0)% RH, at 89 (+− 3)° C. Black Panel Temperature<br>1.0 h light, 95 (+−5.0)% RH, at 38 (+−3)° C. Black Panel Temperature |

The conventional approaches herein have been proven to offer only meager incremental improvements in SLP and still ultimately fail to accurately predict service life in actual end-use environments for most materials. The solution to accurate SLP, therefore, remains not obvious.

As may be observed from the table above, conventional artificial or laboratory weathering devices have simple control algorithms that monitor and maintain a temperature, irradiance or humidity at a single set point for a period of time. The duration of the specific variable and the absolute settings of the variable are typically determined by standards committees referenced in part above and as known by one of ordinary skill in the art. The ASTM standards for xenon arc and fluorescent weathering devices show the very simplistic cycles for different material tests. For example, ASTM G 154-06 sets forth in table X2.1 for fluorescent weathering devices a number of different cycles, all of which simply proscribe a number of exposure hours at a single irradiance and temperature and a number of hours of condensation at a single temperature. SAE J1960 sets forth suggested cycles such as 40 minutes of irradiance at 0.55 $W/m^2$, at 70° C. black standard temperature followed by 20 minutes of irradiance at 0.55 $W/m^2$, at 70° C. with a water spray on specimens, followed by another 60 min of irradiance at the same light and temperature settings, followed by 60 min of dark at 38° C. ASTM G 26 sets forth the same exposure cycle philosophy using specific static set points for specific durations of time. As further examples, FIG. 1 is a graphical representation of the step function of the ASTM G 155, cycle 8 irradiance exposure cycle, and FIG. 2 is a graphical representation of the step function of the ASTM G 155, cycle 8 temperature exposure cycle. These cycles were developed in consensus standards committees and have little resemblance to the end-use environment cycles they were intended to simulate.

These conventional approaches do not consider that the natural end-use environment has significantly different cycles than could be produced by conventional artificial or laboratory weathering devices. Cycles observed in the natural end-use environment are analog in nature (typically sinusoidal-like) rather than step functions as used by conventional approaches and devices. Because of such differences, obtaining good correlation between the two exposure results (i.e., artificial versus natural end-use environments) is very difficult or impossible for many types of materials and products. The reason for this is that the conventional exposure simulation in the laboratory weathering device with an artificial light source poorly simulates the end-use environment variable exposure cycles, and as a result poorly simulates the degradation effects observed on such materials and products in end-use environments. Therefore, material exposure tests using conventional artificial weathering device cycles set by standards committees fail to achieve accurate service life prediction of materials exposed to end-use environment cycles.

Conventional artificial weathering approaches also do not account for reciprocity effects in material degradation. Deviations from reciprocity often occur in materials when exposure at a low irradiance results in a different effect than irradiance at higher levels even when the exposure results in the same radiant energy, as further described in US Publication No. 2005/0120811 A1, which is incorporated herein by reference. Conventional artificial weathering approaches and devices use exposures timed on a UV radiant energy basis (the product of UV irradiant intensity and time) with irradiance set at a single level or step measured in $J/m^2$ UV. Likewise, end-use exposures are also timed and measured by UV radiant energy. However, this is an erroneous approach to SLP, because the cumulative degradation effect from a natural end-use environment cycle of varying UV intensity will be very different than the cumulative degradation effect observed in an artificial weathering device from an artificial cycle at a single UV intensity even though both the exposures are conducted to the same aggregate amount of UV radiant energy exposure. Difficulty in obtaining the same degradation results with identical materials exposed for the same aggregate UV radiant exposure regardless of artificial exposure or natural exposure points to a major disadvantage with the conventional approach.

Co-variables with light intensity, material temperature and moisture also differ significantly between conventional artificial weathering approaches and observed end-use environment cycles. Material exposure temperatures are a complex function of material characteristics such as solar absorbance, emittance and thermal conductivity characteristics of the material as well as environmental variable characteristics such as ambient temperature, wind velocity, solar intensity, sky temperature and material orientation characteristics. Because the end-use environment variable characteristics are always changing, the dynamic nature of ever-changing environmental variables results in very different material degradation observed in end-use environments compared with observations in artificial weathering approaches and devices which hold exposures at fixed, step function set points. For example, it is well known that varying the temperature of reacting materials can vary chemical reaction rates. A dynamic end-use temperature environment, therefore, can be expected to produce a different cumulative material degradation than conventional artificial laboratory weathering approaches or devices that hold a single temperature step function.

Exposure temperature is a co-variable with light intensity; accordingly, there is an opportunity for a meta-level interaction between reciprocity effects and chemical reaction rates affected by temperature. Temperature and moisture variables also interact given that diffusion rates are controlled by temperature. Therefore, moisture ingress into materials on natural exposures are a complex function of environmental moisture (rain, condensation, humidity, etc.), and material temperature, which, in turn is a complex function of solar irradiant intensity interacting with ambient temperatures and other environmental variables. The buildup and interplay of lower and higher order variable effects on material degradation occurring in the natural diurnal and seasonal end-use environment cycles cannot be simulated by simple, single set point step function settings in conventional artificial weathering devices or operational approaches.

Therefore, there is a need for new and non-obvious methods and apparatus for accurate service life prediction of materials that do not require exposure cycles that have little resemblance to the natural end-use environment cycles they were intended to simulate; have difficulty in obtaining the same degradation results with identical materials; work in a limited sense for some materials but not at all for other materials; have a cumulative degradation effect very different than the cumulative degradation effect observed from a natural end-use environment cycle; fail to account for the buildup and interplay of lower and higher order variable effects on material degradation occurring in the natural diurnal and seasonal end-use environment cycles; rudimentary operating approaches, such as, fixed step functions that are unrelated to natural end-use environment cycles.

The subject disclosure is directed to a new, non-obvious and improved methods and apparatus that overcome all of the herein identified problems and disadvantages, and others, and provides an optimal approach for accurate SLP methods and apparatus that faithfully predict material performance in selected or desired micro-environment cycles and faithfully reproduce selected or desired micro-environment cycle characteristics.

BRIEF DESCRIPTION OF THE DRAWINGS

The following disclosure as a whole may be best understood by reference to the provided detailed description when read in conjunction with the accompanying drawings, drawing description, abstract, background, field of the disclosure, and associated headings. Identical reference numerals when found on different figures identify the same elements or a functionally equivalent element. The elements listed in the abstract are not referenced but nevertheless refer by association to the elements of the detailed description and associated disclosure.

FIG. 1 is a graphical representation of a conventional irradiance exposure cycle.

FIG. 2 is a graphical representation of a conventional temperature exposure cycle.

FIG. 3 is a perspective view of one of the methods in accordance with one embodiment of the present disclosure.

DETAILED DESCRIPTION

Figure 4:
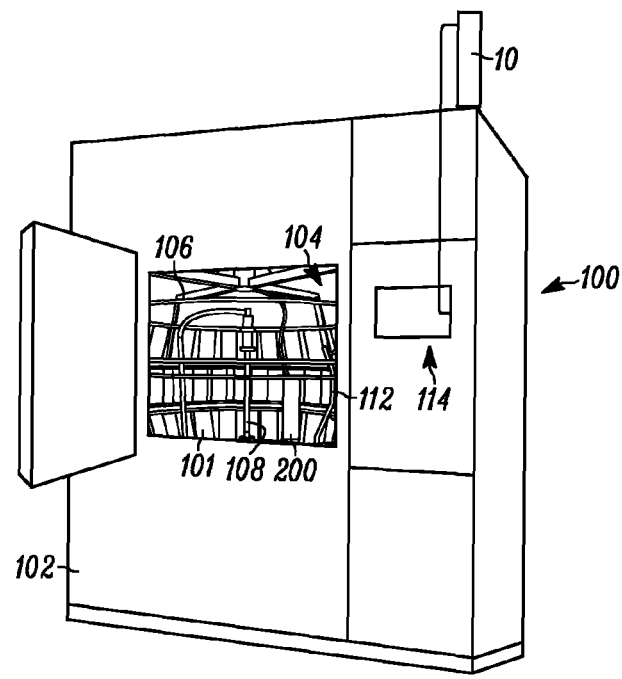
FIG. 4 is a perspective view of an accelerated weathering test apparatus in accordance with one embodiment of the methods and apparatus of the present disclosure.

The present disclosure is not limited to the particular details of the apparatus depicted, and other modifications and applications may be contemplated. Further changes may be made in the apparatus, device or methods without departing from the true spirit of the scope of the disclosure herein involved. It is intended, therefore, that the subject matter in this disclosure should be interpreted as illustrative, not in a limiting sense.

In one aspect of the present disclosure, a method for accurate service life prediction may include controlling an accelerated weathering test apparatus that may have a test chamber, a mount in the test chamber for a test specimen, an irradiance source in the test chamber, a temperature adjustment source in the accelerated weathering test apparatus, a moisture adjustment source in the accelerated weathering test apparatus. A controller may be connected to the irradiance source, temperature adjustment source and moisture adjustment source and may include a processor and a memory that stores programming instructions, that when executed by the processor, causes the controller to function to operate. The method may include recording operating parameters of a multi-variable micro-environment cycle; exposing the test specimen to the multi-variable micro-environment cycle in the test chamber in accordance with the operating parameters; monitoring the exposure of the test specimen to the multi-variable micro-environment cycle in the test chamber to generate run-time variables; and adjusting the programming instructions so that the run-time variables reconcile to the operating parameters.

In another aspect of the present disclosure, an accelerated weathering test apparatus for accurate service life prediction by exposing a test specimen to operating parameters of a multi-variable micro-environment cycle recorded in-situ may include a test chamber; a mount for supporting a test specimen; an irradiance source in the test chamber; a temperature adjustment source in the accelerated weathering test apparatus; and, a moisture adjustment source in the accelerated weathering test apparatus. The controller may be connected to the irradiance source, temperature adjustment source and moisture adjustment source and may include programming instructions and a processor to execute the programming instructions to cause the controller to function to: expose the test specimen to the multi-variable micro-environment cycle in the test chamber in accordance with the operating parameters; monitor the exposure of the test specimen to the multi-variable micro-environment cycle in the test chamber to generate run-time variables; and adjust the programming instructions so that the run-time variables reconcile to the operating parameters.

In yet another aspect of the present disclosure, a method for accurate service life prediction may include controlling an accelerated weathering test apparatus that may have a test chamber, a mount in the test chamber for a test specimen, an irradiance source in the test chamber, a temperature adjustment source in the accelerated weathering test apparatus, a moisture adjustment source in the accelerated weathering test apparatus. A controller may be connected to the irradiance source, temperature adjustment source and moisture adjustment source and may include a processor and a memory that stores programming instructions, that when executed by the processor, causes the controller to function to operate. The method may include generating, by the processor, function parameters that model the multi-variable micro-environment cycle; exposing the test specimen to the multi-variable micro-environment cycle in the test chamber in accordance with the operating parameters; monitoring the exposure of the test specimen to the multi-variable micro-environment cycle in the test chamber to generate run-time variables; and adjusting the programming instructions so that the run-time variables reconcile to the operating parameters.

In still yet another aspect of the present disclosure, an accelerated weathering test apparatus for accurate service life prediction by exposing a test specimen to a multi-variable micro-environment cycle may include a test chamber; a mount for supporting a test specimen; an irradiance source in the test chamber; a temperature adjustment source in the accelerated weathering test apparatus; and, a moisture adjustment source in the accelerated weathering test apparatus. The controller may be connected to the irradiance source, temperature adjustment source and moisture adjustment source and may include programming instructions and a processor to execute the programming instructions to cause the controller to function to: generate, by the processor, function parameters that model an in-situ multi-variable micro-environment cycle; expose the test specimen to the multi-variable micro-environment cycle in the test chamber in accordance with the function parameters; monitor the exposure of the test specimen to the multi-variable micro-environment cycle in the test chamber to generate run-time variables; and adjust the programming instructions so that the run-time variables reconcile to the function parameters.

In a further aspect of the present disclosure, the methods and apparatus may include operating parameters that are at least two selected from the group consisting of temperature, ultraviolet irradiance and moisture.

In a still further aspect of the present disclosure, the methods and apparatus may include editing the operating parameters after recording the operating parameters. For example, editing the operating parameters may include removing non-critical time periods of the operating parameters from the multi-variable micro-environment cycle, adjusting the operating parameters with respect to one of the group consisting of frequency, duration and sequence, averaging a plurality of micro-environment cycles or generating a statistically probable worst case scenario.

In yet another aspect of the present disclosure, the methods and apparatus may include recording operating parameters with a micro-environment detector, positioning an exposure detector in the test chamber and/or connecting the micro-environment detector to the controller. As an example, the micro-environment detector and the exposure detector may be both calibrated to a common operational specification, may be a same device or may be identical devices.

In yet still another aspect of the present disclosure, the methods and apparatus may include the multi-variable micro-environment cycle as an outdoor micro-environment, an indoor micro-environment or a laboratory-generated micro-environment.

In a still yet further aspect of the present disclosure, the methods and apparatus may include operating parameters and/or function parameters having generally smooth continuous rates of change that may also include intermittent non-continuous rates of change.

The present disclosure sets forth new, non-obvious and improved methods and apparatus that overcome the problems and disadvantages described herein and provide accurate SLP methods and apparatus that faithfully reproduce selected or desired micro-environment cycles or characteristics of such cycles. The optimal methods and apparatus of the present disclosure are based on and derived from a fundamental understanding, application and incorporation of and accounting for two distinct sets of characteristics—(a) two characteristics of all materials, and (b) two characteristics of all end-use environments.

The first material characteristic is a material's reciprocity behavior (or deviation from strict reciprocity), as described above and incorporated herein from US Publication No. 2005/0120811 A1. The methods and apparatus in this disclosure account for reciprocity effects in material degradation. Deviations from reciprocity can be accounted for in the apparatus and methods of this disclosure by accurately simulating the frequency, duration and sequence of exposure, such as, for example, at a low irradiance and irradiance at higher levels, or any other operating or function parameters. A major advantage of the present disclosure is obtaining the same degradation results for identical materials or test specimens regardless if exposed to artificial or laboratory accelerated exposure cycles or natural end-use multi-variable micro-environment exposure cycles by generating exposures in the artificial accelerated weathering test apparatus that are an accurate simulation of the natural multi-variable micro-environment cycles (i.e., exposing the test specimen to the same operating or function parameters of a natural multi-variable micro-environment cycle within the accelerated weathering test apparatus). One reason for such advantages is that both exposures are matched to equivalent UV radiant exposures ($KJ/m^2$ UV) (i.e., the operating or function parameters of the natural end-use micro-environment exposure include, in party, a variety of UV intensities from low to high throughout the cycle and the artificial accelerated weathering test apparatus exposure also includes the same proportion of varieties of UV intensities for the same frequencies, durations and sequences). Because of reciprocity effects, specifically the apparent departure from reciprocity observed for many materials, the cumulative degradation effect from a natural end-use multi-variable micro-environment cycle of varying UV intensity may be very closely simulated to produce an accurate cumulative degradation effect or SLP observed in an artificial or laboratory accelerated weathering test apparatus using the methods and apparatus of the present disclosure. Conventional weathering approaches and devices fail to properly understand, apply, incorporate or account for this first material characteristic.

The second material characteristic is the fact that different weathering variables interact to highly effect material degradation rates in non-obvious and non-intuitive manners. Characterization of the effect of interacting variables on materials degradation rates is so complex, it requires sophisticated statistically designed experiments generating empirical data for characterization. Since the apparatus and methods of this disclosure provide such accurate end-use multi-variable micro-environment cycle simulation, the co-variables with light intensity, material temperature and moisture will also be accurately simulated in the artificial accelerated weathering test apparatus exposure cycle of the present disclosure. The run-time variables (e.g., temperature, UV irradiance, moisture, etc.) of the artificial accelerated weathering test apparatus exposure cycle of the present disclosure are always changing in the same manner and with the same generally smooth continuous rates of change as in the operating or function parameters of the desired or selected multi-variable micro-environment cycles (e.g., frequency, duration, sequence, etc.). Accordingly, the dynamic nature of ever-changing run-time variables results in a very similar material degradation as observed in the operating or function parameters of end-use multi-variable micro-environment cycles. For example, the complex end-use variation in chemical reaction rates of a multi-variable micro-environment can be re-created in an artificial laboratory accelerated weathering test apparatus using the apparatus and methods of this disclosure, such as by playing back or exposing a test specimen to the recorded operating parameters or generated function parameters of the desired or selected multi-variable micro-environment cycles, monitoring such exposure to generate run-time variables (i.e., observed exposures within the accelerated weather test apparatus by an exposure detector) and adjusting the play-back to reconcile to the operating or function parameters, can be expected to produce the same cumulative material degradation as a dynamic natural end-use multi-variable micro-environment cycle.

The complex interaction of temperature and moisture operating parameters can also be accurately simulated by the apparatus and methods of this disclosure, as well as, the resulting diffusion rates controlled by temperature as described by Fick (see Crank, J. Park, G S, "Measurement Methods" in Crank, J. Park, G S (eds.) Diffusion in Polymers, pp. 1-2, Academic Press, New York, 1968) and Einstein (see Ghez, R. "A Primer of Diffusion Problems" pp. 86-87, John Wiley & Sons, New York, 1988) by recreating the complex co-variable operating or function parameters of end-use multi-variable micro-environment cycles recorded in the outdoor end-use environment or generated to simulate the same. Artificial accelerated weathering test apparatus implementing the apparatus and methods of this disclosure may also simulate the buildup and interplay of lower and higher order variable effects on material degradation from natural end-use multi-variable micro-environment cycles. Conventional weathering approaches and devices fail to properly understand, apply, incorporate or account for this second material characteristic.

The first general environmental characteristic is the generally smooth and continuous rates of change of operating or function parameters (e.g., sinusoidal nature, first derivative, trigonometric, etc.) of the end-use multi-variable micro-environment cycle (e.g., UV, temperature, moisture). That is, at some points in time of an end-use micro-environment weathering exposure, any one of the operating or function parameters may be at a low level while at other points in time of end-use micro-environment weathering exposure, any one of the operating or function parameters may be at a high level. A diurnal or seasonal temperature cycle or an annual irradiance cycle demonstrates this characteristic. Conventional weathering approaches and devices fail to properly understand, apply, incorporate or account for this first general environmental characteristic.

The second general environmental characteristic is the intermittent non-continuous rates of change or chaotic nature of the operating or function parameters. For example, when a cloud blocks UV sunlight from reaching a material surface, a cold front moves into the local area dropping material exposure temperatures, a body of moist air moves over, winds change the material's exposure temperature, etc. Conventional weathering approaches and devices fail to properly understand, apply, incorporate or account for this second general environmental characteristic.

These four above described complex characteristics: (a) materials reciprocity response to different levels of operating or function parameters; (b) the interacting effect of different operating or function parameters effecting material degradation rates; (c) the cyclic nature of operating or function parameters resulting in different levels of different operating or function parameters at different points in time; and (d) the chaotic nature of operating or function parameter levels, all interplay to result in unique material degradation rates dependent on material (i.e., test specimen) and multi-variable micro-environment characteristics. Current SLP approaches and devices do not simulate this complexity of levels of multi-variable micro-environment cycles throughout test specimen exposure time in artificial accelerated weathering test apparatus and methods and, therefore, fail to achieve accurate SLP for varieties of materials. For example, a conventional approach may proscribe a segment of a current test method to be run with a 0.65 W/m$^2$ UV irradiance while holding the material temperature at 60° C. for 8 hours before moving to the next segment of the approach. Such irradiance and temperature level settings being representative of general average end-use environment measurements. However, the non-obvious reality of the end-use environment is that a steady state of 0.65 W/m$^2$ and 60° C. is rarely (if ever) actually achieved for even short time periods, let alone for hours. The diurnal cycle alone forces ever changing levels of irradiance and temperature. Chaotic influences of atmosphere like clouds and breezes also vary levels of operating or function parameters within very short time frames. Those changes and the associated rates of change of such operating or function parameters are not simulated by current SLP approaches or devices. However, the effects of those operating or function parameter changes (and the associated rates of such changes) have a profound influence on material degradation rates over long term end-use exposure.

For another example, a material exposed to low irradiance of UV in the morning end-use environment will have a different apparent quantum efficiency than a high irradiance exposure near solar noon (i.e., reciprocity difference) resulting in different contributions to buildup of a material's long term degradation not accounted for in current SLP approaches and devices. For yet another example, a very high irradiance (e.g., 0.65 W/m$^2$ UV) exposure in winter time during a period of very cold temperatures (e.g., 0° C.) will result in a very different interactive effect of irradiance and temperature resulting in a different contribution to buildup of a materials long term degradation than a lower irradiance (e.g., 0.35 W/m$^2$) at a higher temperature (e.g., 10° C.) which may happen the very next day in an end-use exposure, but is not accounted for in current SLP approaches and devices.

For still another example, an anomalous change (and associated rate of change) from a high irradiance and high temperature exposure to a low irradiance with low temperature exposure due to a cloud passing between the sun and a material in end-use exposure would not be simulated in conventional artificial weathering SLP approaches and devices, yet over long term end-use exposure, the cumulative effect of these types of changes (and the associated rates of change) significantly effect a material's service life.

Over the long term of conventional artificial weathering exposure approaches, these simulation errors build up and result in the predicted service life that is significantly different than the observed service life of the same material in end-use environments. Accordingly, conventional SLP approaches and devices fail to meet researcher needs, since the conventional approaches and devices fail to simulate the changes (and the associated rates of change) of end-use multi-variable micro-environment cycles, and instead focus on obvious fixed, step function levels of exposure merely representing gross averages of end-use exposures. It is the simultaneous changes of multiple operating or function parameters, as described by first derivative calculus (i.e., the rate of such changes), that are critical to characterizing materials degradation in end-use micro-environment cycles—but which are not properly understood, applied, incorporated or accounted for in conventional SLP approaches and devices.

By way of example and not limiting in any sense, the present disclosure methods and apparatus in one embodiment are directed to recording operating parameters of multi-variable micro-environment cycles, including, but not limited to, solar UV irradiance, temperature and moisture exposure conditions with a micro-environment detector or data logger and then playing back the recorded operating parameters using an artificial accelerated weathering test apparatus including irradiance (other than solar), temperature adjusting and moisture adjusting sources, an exposure detector or data logger in the test chamber as a feedback device and a controller to ensure very accurate simulation of the end-use multi-variable micro-environment cycles inside the artificial accelerated weathering test apparatus so that the degradation of the test specimen exposed inside the artificial accelerated weathering test apparatus is accurately simulated.

By way of example and not limiting in any sense, the present disclosure methods and apparatus in another embodiment are directed to generating function parameters that model in-situ multi-variable micro-environment cycles, including, but not limited to, UV irradiance, temperature and moisture exposure conditions and then playing back the generated function parameters using an artificial accelerated weathering test apparatus including irradiance (other than solar), temperature adjusting and moisture adjusting sources, an exposure detector in the test chamber as a feedback device and a controller to ensure very accurate simulation of the end-use multi-variable micro-environment cycles inside the artificial accelerated weathering test apparatus so that the degradation of the test specimen exposed inside the artificial accelerated weathering test apparatus is accurately simulated.

Conventional SLP approaches and devices do not record the operating parameters of complex multi-variable micro-environment cycles or generate function parameters that model in-situ multi-variable micro-environment cycles and reproduce such cycles inside an artificial accelerated weathering test apparatus; use a micro-environment detector and then use an exposure detector inside the artificial accelerated weathering test apparatus to measure the run-time variables inside the artificial accelerated weathering test apparatus in order to control the run-time variables, thus ensuring an accurate simulation of the operating or function parameters in the artificial accelerated weathering test apparatus, wherein the micro-environment detector and the exposure detector are the "same;" edit the operating or function parameters before reproduction of such cycles in the accelerated weathering test apparatus in order to achieve an accelerated test while still maintaining the basic micro-environment cycle characteristics for accurate simulation of material degradation in end-use.

As a result, such embodiments more accurately simulate the degradation of materials in end-use micro-environments than conventional approaches and devices which are limited to over-simplistic fixed step function settings; and capture or characterize unique micro-environment cycle conditions that are associated with specific end-use material degradation or failures observed in end-use environments so that play back of the unique micro-environment cycle exposure conditions can then be used to simulate the exact exposure conditions in the laboratory (i.e., artificial accelerated weathering test apparatus) causing such degradation or failure. Consequently, new material formulations can then be produced and tested in accurate simulations of applicable end-use micro-environment cycles to determine if such new materials will withstand the specific end-use micro-environment cycles that caused such degradation or failure in previously end-use environment exposed materials.

Additionally, such embodiments much more closely simulate the analog nature (e.g., sinusoidal, first derivative, trigonometric, etc.) of the end-use multi-variable micro-environment cycles rather than simplistic fixed step functions of convention approaches and devices, such as, for example only, more closely simulating the sinusoidal nature of diurnal, seasonal or annual irradiance, temperature and moisture variables observed in end-use environments; chaotic anomalies observed in end-use environments, that often result in failure of end-use materials. As a result, the apparatus and methods of the present disclosure provide much better simulation of the end-use degradation effects on materials due to better multi-variable micro-environment cycle simulation. Consequently, the accuracy of service life prediction of the materials is greatly improved over the conventional approaches and devices.

One aspect of the apparatus and methods of this disclosure is to place a micro-environment detector and data logger in an end-use environment to record the actual multi-variable micro-environment cycles and replay, by way of simulation, such cycles back in an artificial laboratory accelerated weathering test apparatus rather than developing highly artificial, over-simplistic fixed step function averaged settings for use in conventional approaches and devices.

Another aspect of the apparatus and methods of this disclosure is to simulate the generally smooth continuous rates of change (e.g., analog, sinusoidal-type cycle, etc.) functions observed in end-use environments rather than a simple fixed step function cycles of conventional approaches and devices to simulate actual end-use environment weathering in an artificial accelerated weathering test apparatus.

Another aspect of the apparatus and methods of this disclosure is to use a micro-environment detector in the end-use environment and exposure detector inside the artificial weathering chamber during play back that are the "same" to insure that the monitored run-time variables within the artificial accelerated weathering test apparatus have great fidelity to the multi-variable micro-environment cycles recorded previously in end-use or generated by modeling a multi-variable micro-environment cycle. Some preferred embodiments of the "same" detector may include the micro-environment detector and the exposure detector both calibrated to a common operation specification (e.g., NIST, etc.), the identical device or the same device, so that small detector to detector differences are not introduced into the play back.

Another aspect of the apparatus and methods of this disclosure is to edit the operating or function parameters to remove non-critical time periods from such operating parameters, supplement the operating parameters for acceleration, adjust the operating parameters with respect to one of the group consisting of frequency, duration and sequence, average a plurality of micro-environment cycles, generate a statistically probable worst case scenario and interpolate the operating parameters to produce a generally smooth continuous rate of change. For example, such editing may include maintaining the same dynamic multi-variable micro-environment cycle with an offset, multiplying the multi-variable micro-environment cycle by a constant to increase amplitude for acceleration while still maintaining the dynamic of the multi-variable micro-environment cycle or modify the multi-variable micro-environment cycle in other known or obvious desirable ways, such as true calculus-based, differential and integral tools can be applied to the multi-variable micro-environment cycle and controller functions in the artificial accelerated weathering test apparatus to produce new simulation and acceleration methods and represents a dramatic departure from conventional approaches and devices.

FIG. 3 is a perspective view of one aspect of the methods for accurate service life prediction in accordance with one embodiment of the present disclosure wherein the operating parameters of a multi-variable micro-environment cycle are recorded. In one embodiment, the operating parameters are at least two selected from the group consisting of temperature, UV irradiance and moisture. However, one of ordinary skill in the art will recognize that the operating parameters may be any suitable micro-environment variable that may be recorded and may be useful in connection with the intended purpose of the present disclosure. Preferably, recording the operating parameters of the multi-variable micro-environment cycle includes a micro-environment detector connectable to a controller of the accelerated weathering test apparatus as described herein. The micro-environment detector may include any suitable multi-variable exposure measuring device or sensor (e.g., irradiance, temperature, moisture, etc.) that may be connected by wired or wireless connection to the controller of the accelerated weathering test apparatus in order to log or record the desired or selected operating parameters, such as, for example only, by any suitable apparatus or device that has a single memory, a plurality of memory locations, shared memory, CD, DVD, ROM, RAM, optical storage, microcode, data store, memory, read-only memory, random access memory, rewriteable disc memory, write-once-read-many disc memory, electrically or electronically erasable programmable ROM (EEPROM), holographic memory, remote storage memory, or any other non-volatile storage suitable memory device for storing date (i.e., operating parameters) in hardware or software form commonly know in the art for use in connection with the present disclosure. The multi-variable micro-environment cycle may be selected from the group consisting of an outdoor micro-environment, an indoor micro-environment and a laboratory-generated micro-environment. FIG. 3 illustrates various implementations of one aspect of the present disclosure. A micro-environment detector 10 may be installed in any imaginable location in order to record a desired or selected micro-environment cycle for a certain material, such as, for example only, on an exterior surface 22 of a building 20, such as a roof 24 or a wall 26, on an interior surface of the building 20, such as a frame of an exterior window 28 of the building 20, the interior walls or the floor, on continuously or non-continuously exposed components 30 of the building 22 structure, such as deck or porch railing, on an exterior surface 42 of a vehicle 40, on an interior surface 44 of the vehicle 40, such as the dash, seats, carpet, etc., an continuously or non-continuously exposed surface of a sign 50 or any other suitable or imaginable installation in accordance with the intended purpose of the present disclosure. Additionally, the micro-environment detector 10 may be installed in an accelerated weathering test apparatus (such as or similar to the apparatus described herein, but recognized by one of ordinary skill in the art to be any other similar or suitable such apparatus) to record the laboratory-generated micro-environment generated therein in the same manner as described herein.

Figure 6:
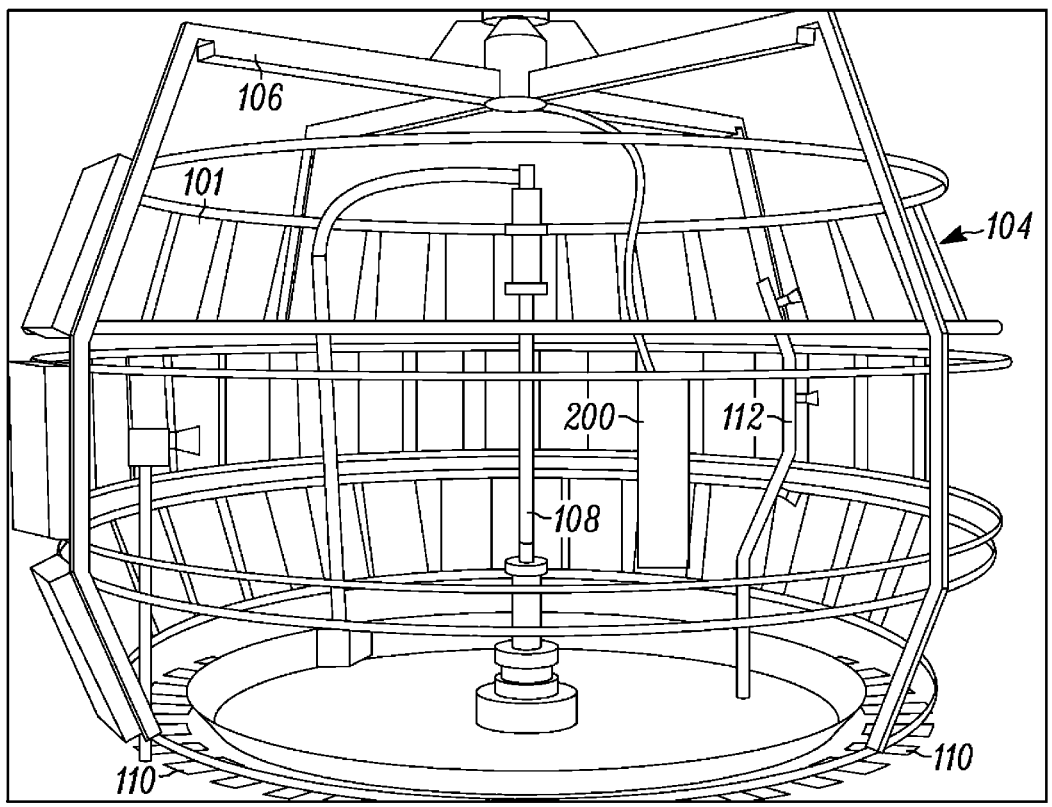
FIG. 6 is a detailed view of an accelerated weathering test apparatus in accordance with one embodiment of the methods and apparatus of the present disclosure.

FIG. 4 is a perspective view of an accelerated weathering test apparatus 100 and FIG. 6 is a detailed view of the accelerated weathering test apparatus 100, both in accordance with one embodiment of the present disclosure for accurate service life prediction by exposing a test specimen 101 to operating parameters or a multi-variable micro-environment cycle recorded in-situ as described herein. The accelerated weathering test apparatus 100 may include a test chamber 104 defined in the housing 102, a mount 106 disposed in the test chamber 104, an irradiance source 108 disposed in the test chamber 104, a temperature adjustment source 110 disposed in the accelerated weathering test apparatus 100 and in communication with the test chamber 104, a moisture adjustment source 112 disposed in the accelerated weathering test apparatus 100 and in communication with the test chamber 104, and a controller 114 connected to the irradiance source 108, temperature adjustment source 110 and moisture adjustment source 112 including a processor and a memory that stores programming instructions, that when executed by the processor, causes the controller 114 to function to: expose the test specimen 101 to the multi-variable micro-environment cycle in the test chamber 104 in accordance with the operating parameters; monitor the exposure of the test specimen 101 to the multi-variable micro-environment cycle in the test chamber 104 to generate run-time variables; and adjust the programming instructions so that the run-time variables reconcile to the operating parameters.

In one embodiment, the irradiance source 108 may include any suitable artificial, non-solar, light source, such as, for example only, xenon arc, fluorescent or similar lamps, with or without filters, or any other suitable light source that may be commonly known and used in the art for weathering purposes, so that the irradiance exposure in the test chamber 104 may be adjusted up, down or the same based on the operating or function parameters under instruction from the controller 114. In one embodiment, the temperature adjusting source 110 may include any combination of heating (e.g. direct or indirect heat source), cooling (e.g., direct or indirect cooling source) and air movement (e.g., fan, ducting, dampers, mixing devices or other air moving devices) components as commonly known as suitable for the intended application in the accelerated weathering art, so that the temperature exposure in the test chamber 104 may be adjusted up, down or the same based on the operating or function parameters under instruction from the controller 114. In one embodiment, the moisture adjusting source 112 may include any combination of fluid discharge (e.g., fluid source and discharge devices) and air movement (e.g., fan, ducting, dampers, mixing devices or other air moving devices) components as commonly known as suitable for the intended application in the accelerated weathering art, so that the moisture exposure in the test chamber 104 may be adjusted up, down or the same based on the operating or function parameters under instruction from the controller 114. The structure and associated functionality of each of the irradiance source 108, temperature adjusting source 110 and moisture adjusting source 112 are described in more detail in the commonly owned U.S. Pat. Nos. 7,038, 196; 6,946,652; 6,872,936; 6,720,562; 5,646,358; and 5,503, 032; and US Publication Nos. 20100005911; 20070295114; and 20050167580; that are each individually and collectively incorporated herein by reference.

In one embodiment, the controller 114 may be configured as any suitable device, in hardware or software form, that communicates with inputs (i.e., micro-environment detector 10 or sub-controller or editing device) and outputs (i.e., irradiance source 108, temperature adjusting source 110 and moisture adjusting source 112), such as a programmable logic controller comprising a processor and memory that stores the programming instructions. Other suitable controllers may be used, for example only and not in any limiting sense, a processing module including a processor and memory to facilitate management of the operations of the processing module. The processor may be a microprocessor, central processing unit or micro-controller, application-specific integrated circuit, field programmable gate array, digital signal processor, micro-controller or any other suitable processing device. If the processor is a microprocessor, it may be a "Pentium," "Power PC," or any other suitable microprocessor, CPU or micro-controller commonly known in the art. The memory may be any suitable apparatus or device that has a single memory, a plurality of memory locations, shared memory, CD, DVD, ROM, RAM, optical storage, microcode, data store, memory, read-only memory, random access memory, rewriteable disc memory, write-once-read-many disc memory, electrically or electronically erasable programmable ROM (EEPROM), holographic memory, remote storage memory, or any other non-volatile storage suitable memory device for storing data (i.e., operating or function parameters) in hardware or software form commonly know in the art for use in connection with the present disclosure. In one embodiment, the processor may include one or more processing devices including any combination of any of the foregoing capable of executing the programming instructions and operating upon the stored data. The memory includes executable instructions that are executed by the processor and data, as well as, programming variables or any other suitable programming source code or object code commonly known in the art that may be embodied in any suitable format such as a hard drive, cache memory, etc. In one embodiment, the controller 114 may include a user input device (e.g., keyboard, mouse, touch screen, microphone and suitable voice recognition application or any other means whereby a user of the controller 114 may provide input data to the processor), a display (e.g., cathode ray tube, flat panel display or any other display mechanism known to those of ordinary skill in the art) and a peripheral interface (e.g., hardware, firmware and/or software necessary for communication with various input and output devices (e.g., micro-environment detector 10, exposure detector, irradiance source 108, temperature adjusting source 110 and moisture adjusting source 112, media drives (e.g., magnetic disk or optical disk drives, flash drives, etc. which may be used to read storage media comprising the executable instructions used to implement, in one embodiment, the methods described herein) or any other source of input or output useful in connection with the present disclosure (e.g., a network interface comprised of hardware, firmware and/or software that allows the processor to communicate with other devices via wired or wireless networks, whether local or wide area, private or public, as known in the art).

Figure 7:
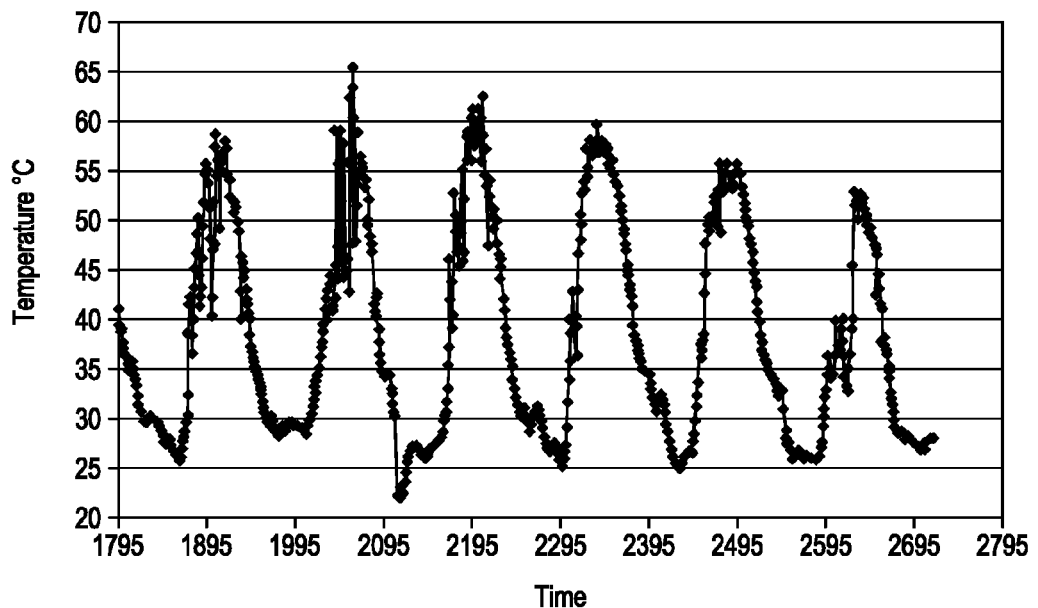
FIG. 7 is a graphical representation of an operating or function parameter of a multi-variable micro-environment cycle.
Figure 8:
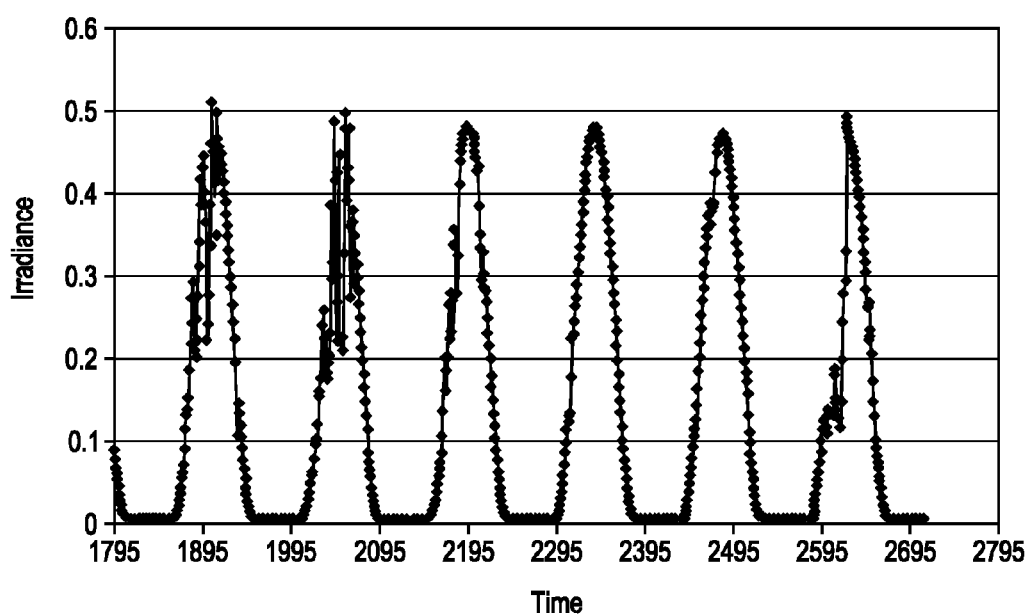
FIG. 8 is a graphical representation of an operating or function parameter of a multi-variable micro-environment cycle.

In one embodiment, the test specimen 101 is exposed to the multi-variable micro-environment cycle in the test chamber 104 in accordance with the operating parameters. For example, FIGS. 7 and 8 are graphical representations of two operating parameters (FIG. 7—temperature, and FIG. 8—irradiance) of a multi-variable micro-environment cycle. The controller 114 operates at least the irradiance source 108 and temperature adjusting source 110 in accordance with the operating parameters (i.e., as programming instructions, stored data, imported instructions, data from the micro-environment detector 10 or editing or sub-controller device as described herein, any other suitable form, mechanism, device or technique, etc.) to recreate such operating parameters in the test chamber 104. An exposure detector 200 may be disposed on the mount 106 in the test chamber 104, just as a test specimen 101, in order to monitor the exposure of the test specimen 101 to the multi-variable micro-environment cycle in the test chamber 104. The micro-environment detector 10 and exposure detector 200 may be the "same" which may include both calibrated to a common operation specification (e.g., NIST, etc.), the identical device or the same device, so that small detector to detector differences are not introduced into the play back. The exposure detector 200 may be connected to the controller 114 by wired or wireless connection in order that run-time variables generated by the exposure detector 200 as representative of the monitored multi-variable micro-environment cycle in the test chamber 104 may be transmitted to the controller 114. In one embodiment, the programming instructions may be adjusted so that the run-time variables reconcile to the operating parameters in order to maintain high fidelity between the two for the advantages described herein.

Figure 5:
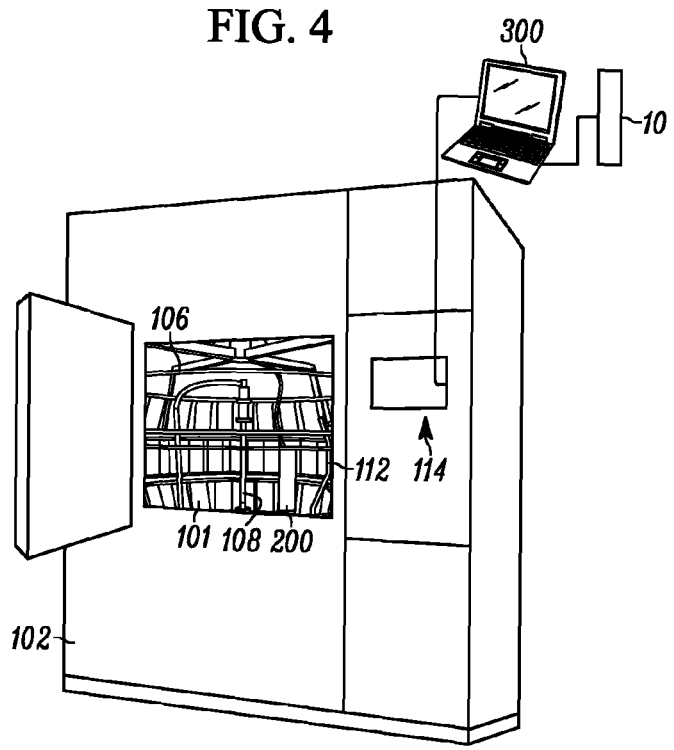
FIG. 5 is a perspective view of an accelerated weathering test apparatus in accordance with one embodiment of the methods and apparatus of the present disclosure.

FIG. 5 is a perspective view of an accelerated weathering test apparatus 100 in accordance with one embodiment of the present disclosure. This embodiment is substantially the same as described herein save that an sub-controller device 300 is connected (i.e., wired or wireless link) with the micro-environment detector 10 and the controller 114. It is within the present disclosure that the sub-controller or editing device 300 may be configured the same as or similar to the controller 114, as described herein (additionally including, without limitation, as hardware, firmware or software, personal computer, etc.), and as a free standing device (e.g., connected to the micro-environment detector 10 and controller 114 by wired or wireless communication, as desired or advantageous) or the functionality of same integrated into the micro-environment detector 10 or controller 114 as desired or advantageous. In one embodiment, the sub-controller device 300 facilitates editing of the operating parameters and the generating of the function parameters. The editing functionality may include editing the operating parameters after recording the operating parameters, which may also be used for generating the function parameters. For example, editing the operating parameters may include removing non-critical time periods of the operating parameters from the multi-variable micro-environment cycle, adjusting the operating parameters with respect to one of the group consisting of frequency, duration and sequence, averaging a plurality of micro-environment cycles or generating a statistically probable worst case scenario. Function parameters may be generated by the processor to model an in-situ multi-variable micro-environment cycle in any manner commonly known in the art from either a theoretical perspective (e.g., Duffey and Beckman-type equations) or observed data, as described herein.

Figure 9:
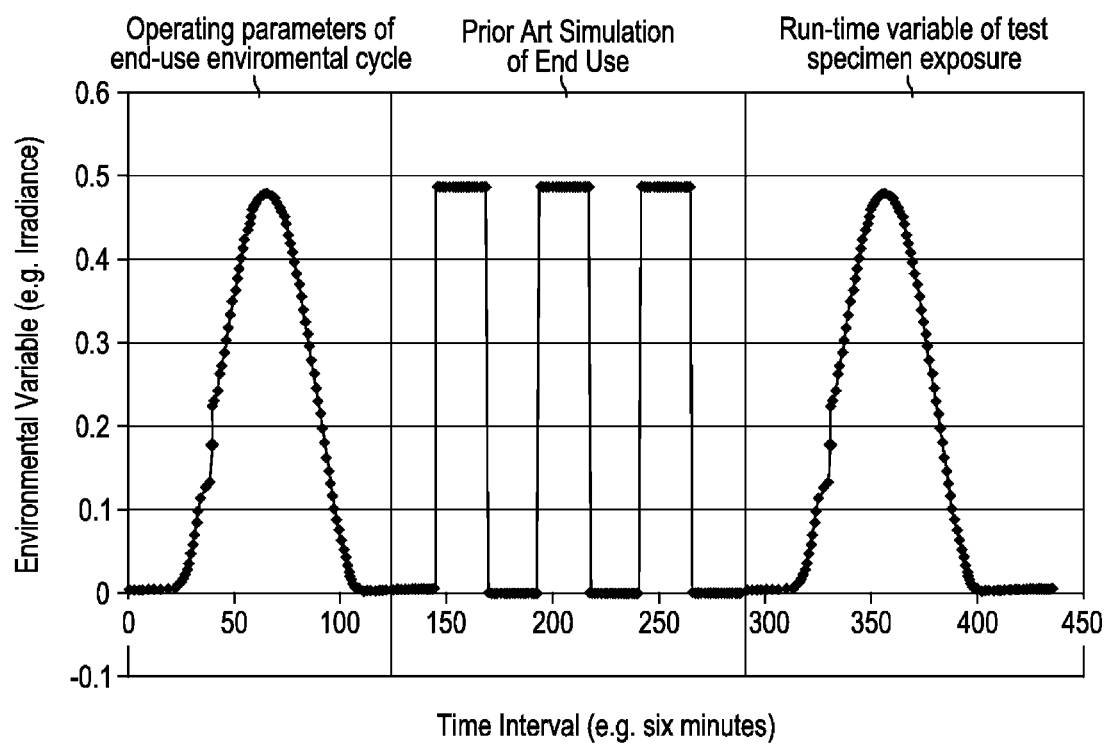
FIG. 9 is a graphical representation of an operating or function parameter of a multi-variable micro-environment cycle, a prior art simulation of such operating or function parameter and a run-time variable of a test specimen exposure in accordance with the present disclosure.

FIG. 9 is a graphical comparison of an operating parameter of an multi-variable micro-environment cycle, a conventional fixed step-function approach and accelerated weathering test apparatus simulation of such operating parameter and a monitored run-time variable of a test specimen exposure in accordance with the present disclosure. One of skill in the art will recognize the high fidelity of the run-time variable to the operating parameter (and the resultant service life predictability advantages described herein), as distinguished from the conventional approach (which is fraught with all the disadvantages and unpredictability described herein).

The preceding detailed description merely sets forth some examples and embodiments of the present disclosure and that numerous changes to the disclosed embodiments can be made in accordance with the disclosure herein without departing from its spirit or scope. The preceding description, therefore, is not meant to limit the scope of the disclosure but to provide sufficient disclosure to one of ordinary skill in the art to practice the invention without undue burden.

What is claimed is:

1. A method for accurate service life prediction by controlling an accelerated weathering test apparatus including a test chamber, a mount disposed in the test chamber for supporting a test specimen, an irradiance source disposed in the test chamber, a temperature adjustment source disposed in the accelerated weathering test apparatus and in communication with the test chamber, a moisture adjustment source disposed in the accelerated weathering test apparatus and in communication with the test chamber, a controller connected to the irradiance source, temperature adjustment source and moisture adjustment source including a processor and a memory that stores programming instructions, that when executed by the processor, causes the controller to function to operate the irradiance source, temperature adjustment source and moisture adjustment source, the method comprising:
   recording operating parameters of a multi-variable micro-environment cycle;
   exposing the test specimen to the multi-variable micro-environment cycle in the test chamber in accordance with the operating parameters;
   monitoring the exposure of the test specimen to the multi-variable micro-environment cycle in the test chamber to generate run-time variables; and
   adjusting the programming instructions so that the run-time variables reconcile to the operating parameters.

2. The method of claim 1, wherein the operating parameters are at least two selected from the group consisting of temperature, ultraviolet irradiance and moisture.

3. The method of claim 1, further comprising editing the operating parameters after recording the operating parameters.

4. The method of claim 3, wherein editing the operating parameters includes removing non-critical time periods of the operating parameters from the multi-variable micro-environment cycle.

5. The method of claim 3, wherein editing the operating parameters includes adjusting the operating parameters with respect to one of the group consisting of frequency, duration and sequence.

6. The method of claim 3, wherein editing the operating parameters includes averaging a plurality of micro-environment cycles.

7. The method of claim 6, wherein the averaging the plurality of multi-variable micro-environment cycles includes generating a statistically probable worst case scenario.

8. The method of claim 3, wherein editing the operating parameters includes interpolating the operating parameters to produce a generally smooth continuous rate of change.

9. The method of claim 1, wherein recording operating parameters includes a micro-environment detector connectable to the controller.

10. The method of claim 9, wherein monitoring the exposure includes an exposure detector connected to the controller.

11. The method of claim 10, wherein the micro-environment detector and the exposure detector are both calibrated to a common operational specification.

12. The method of claim 10, wherein the micro-environment detector and the exposure detector are a same device.

13. The method of claim 10, wherein the micro-environment detector and the exposure detector are identical devices.

14. The method of claim 1, wherein monitoring the exposure includes connecting an exposure detector to the controller.

15. The method of claim 1, wherein the multi-variable micro-environment cycle is selected from the group consisting of an outdoor micro-environment, an indoor micro-environment and a laboratory-generated micro-environment.

16. The method of claim 1, wherein exposing the test specimen includes operating parameters having generally smooth continuous rates of change.

17. The method of claim 16, wherein the smooth continuous rates of change include intermittent non-continuous rates of change.

18. The method of claim 1, wherein exposing the test specimen includes connecting a micro-environment detector to the controller.

19. An accelerated weathering test apparatus for accurate service life prediction by exposing a test specimen to operating parameters of a multi-variable micro-environment cycle recorded in-situ, the accelerated weathering test apparatus comprising:
   a test chamber;
   a mount disposed in the test chamber for supporting the test specimen;
   an irradiance source disposed in the test chamber;
   a temperature adjustment source disposed in the accelerated weathering test apparatus and in communication with the test chamber;
   a moisture adjustment source disposed in the accelerated weathering test apparatus and in communication with the test chamber;
   the controller connected to the irradiance source, temperature adjustment source and moisture adjustment source including a processor and a memory that stores programming instructions, that when executed by the processor, causes the controller to function to:
   expose the test specimen to the multi-variable micro-environment cycle in the test chamber in accordance with the operating parameters;
   monitor the exposure of the test specimen to the multi-variable micro-environment cycle in the test chamber to generate run-time variables; and
   adjust the programming instructions so that the run-time variables reconcile to the operating parameters.

20. The apparatus of claim 19, wherein the operating parameters are at least two selected from the group consisting of temperature, ultraviolet irradiance and moisture.

21. The apparatus of claim 19, wherein the operating parameters are edited after being recorded.

22. The apparatus of claim 21, wherein non-critical time periods of the operating parameters are removed from the multi-variable micro-environment cycle.

23. The apparatus of claim 21, wherein the operating parameters are adjusted with respect to one of the group consisting of frequency, duration and sequence.

24. The apparatus of claim 21, wherein a plurality of micro-environment cycles are averaged.

25. The apparatus of claim 24, wherein a statistically probable worst case scenario is generated from the averaging.

26. The apparatus of claim 21, wherein a generally smooth continuous rate of change of the operating parameters is generated by interpolation.

27. The apparatus of claim 19, further comprising a micro-environment detector connectable to the controller for in-situ recordation of operating parameters.

28. The apparatus of claim 27, wherein monitoring the exposure includes an exposure detector in the test chamber connected to the controller.

29. The apparatus of claim 28, wherein the micro-environment detector and the exposure detector are both calibrated to a common operating specification.

30. The apparatus of claim 28, wherein the micro-environment detector and the exposure detector are a same device.

31. The apparatus of claim 28, wherein the micro-environment detector and the exposure detector are identical.

32. The apparatus of claim 19, further comprising an exposure detector in the test chamber connected to the controller.

33. The apparatus of claim 19, wherein the multi-variable micro-environment cycle is selected from the group consisting of an outdoor micro-environment, an indoor micro-environment and a laboratory-generated micro-environment.

34. The apparatus of claim 19, wherein exposing the test specimen includes operating parameters having generally smooth continuous rates of change.

35. The apparatus of claim 34, wherein the smooth continuous rates of change include intermittent non-continuous rates of change.

36. A method for accurate service life prediction by controlling an accelerated weathering test apparatus including a test chamber, a mount disposed in the test chamber for supporting a test specimen, an irradiance source disposed in the test chamber, a temperature adjustment source disposed in the accelerated weathering test apparatus and in communication with the test chamber, a moisture adjustment source disposed in the accelerated weathering test apparatus and in communication with the test chamber, a controller connected to the irradiance source, temperature adjustment source and moisture adjustment source including a processor and a memory that stores programming instructions, that when executed by the processor, causes the controller to function to operate the irradiance source, temperature adjustment source and moisture adjustment source, the method comprising:
  generating, by the processor, function parameters that model an in-situ multi-variable micro-environment cycle;
  exposing the test specimen to the multi-variable micro-environment cycle in the test chamber in accordance with the function parameters;
  monitoring the exposure of the test specimen to the multi-variable micro-environment cycle in the test chamber to generate run-time variables; and
  adjusting the programming instructions so that the run-time variables reconcile to the function parameters.

37. The method of claim 36, wherein the function parameters are at least two selected from the group consisting of temperature, ultraviolet irradiance and moisture.

38. The method of claim 36, wherein generating function parameters includes recording, in-situ, operating parameters of the multi-variable micro-environment cycle.

39. The method of claim 38, further comprising editing the operating parameters after recording the operating parameters.

40. The method of claim 39, wherein editing the operating parameters includes removing non-critical time periods of the operating parameters from the multi-variable micro-environment cycle.

41. The method of claim 39, wherein editing the operating parameters includes adjusting the operating parameters with respect to one of the group consisting of frequency, duration and sequence.

42. The method of claim 39, wherein editing the operating parameters includes averaging a plurality of micro-environment cycles.

43. The method of claim 42, wherein the averaging the plurality of multi-variable micro-environment cycles includes generating a statistically probable worst case scenario.

44. The method of claim 39, wherein editing the operating parameters includes interpolating the operating parameters to produce a generally smooth continuous rate of change.

45. The method of claim 38, wherein recording operating parameters includes a micro-environment detector connectable to the controller.

46. The method of claim 45, wherein monitoring the exposure includes an exposure detector connected to the controller.

47. The method of claim 46, wherein the micro-environment detector and the exposure detector are both calibrated to a common operating specification.

48. The method of claim 46, wherein the micro-environment detector and the exposure detector are a same device.

49. The method of claim 46, wherein the micro-environment detector and the exposure detector are identical devices.

50. The method of claim 36, wherein monitoring the exposure includes an exposure detector connected to the controller.

51. The method of claim 36, wherein the multi-variable micro-environment cycle is selected from the group consisting of an outdoor micro-environment, an indoor micro-environment and a laboratory-generated micro-environment.

52. The method of claim 36, wherein exposing the test specimen includes function parameters having generally smooth continuous rates of change.

53. The method of claim 52, wherein the smooth continuous rates of change include intermittent non-continuous rates of change.

54. The method of claim 36, wherein exposing the test specimen includes connecting a micro-environment detector to the controller.

55. An accelerated weathering test apparatus for accurate service life prediction by exposing a test specimen to a multi-variable micro-environment cycle, the accelerated weathering test apparatus comprising:
  a test chamber;
  a mount disposed in the test chamber for supporting the test specimen;
  an irradiance source disposed in the test chamber;
  a temperature adjustment source disposed in the accelerated weathering test apparatus and in communication with the test chamber;
  a moisture adjustment source disposed in the accelerated weathering test apparatus and in communication with the test chamber;
  a controller connected to the irradiance source, temperature adjustment source and moisture adjustment source including a processor and a memory that stores programming instructions, that when executed by the processor, causes the controller to function to:
  generate, by the processor, function parameters that model an in-situ multi-variable micro-environment cycle;
  expose the test specimen to the multi-variable micro-environment cycle in the test chamber in accordance with the function parameters;

monitor the exposure of the test specimen to the multi-variable micro-environment cycle in the test chamber to generate run-time variables; and adjust the programming instructions so that the run-time variables reconcile to the function parameters.

56. The apparatus of claim 55, wherein the function parameters are at least two selected from the group consisting of temperature, ultraviolet irradiance and moisture.

57. The apparatus of claim 55, wherein the function parameters include in-situ recorded operating parameters of the multi-variable micro-environment cycle.

58. The apparatus of claim 57, wherein non-critical time periods of the operating parameters are removed from the multi-variable micro-environment cycle.

59. The apparatus of claim 57, wherein the operating parameters are adjusted with respect to one of the group consisting of frequency, duration and sequence.

60. The apparatus of claim 57, wherein a plurality of micro-environment cycles are averaged.

61. The apparatus of claim 60, wherein a statistically probable worst case scenario is generated from the averaging.

62. The apparatus of claim 57, wherein a generally smooth continuous rate of change is generated by interpolation.

63. The apparatus of claim 55, further comprising a micro-environment detector connectable to the controller for in-situ recordation of operating parameters.

64. The apparatus of claim 63, wherein monitoring the exposure includes an exposure detector in the test chamber connected to the controller.

65. The apparatus of claim 64, wherein the micro-environment detector and the exposure detector are both calibrated to a common operating specification.

66. The apparatus of claim 64, wherein the micro-environment detector and the exposure detector are a same device.

67. The apparatus of claim 64, wherein the micro-environment detector and the exposure detector are identical.

68. The apparatus of claim 55, further comprising an exposure detector in the test chamber connected to the controller.

69. The apparatus of claim 55, wherein the multi-variable micro-environment cycle is selected from the group consisting of an outdoor micro-environment, an indoor micro-environment and a laboratory-generated micro-environment.

70. The apparatus of claim 55, wherein exposing the test specimen includes function parameters having generally smooth continuous rates of change.

71. The apparatus of claim 70, wherein the smooth continuous rates of change include intermittent non-continuous rates of change.

* * * * *